United States Statutory Invention Registration [19]

[11] Reg. Number: H476

Norris [43] Published: Jun. 7, 1988

[54] SYNTHESIS OF 7-AMINO-4,6-DINITROBENZOFUROXAN

[75] Inventor: William P. Norris, Ridgecrest, Calif.

[73] Assignee: The United States of America as represented by the Secretary of the Navy, Washington, D.C.

[21] Appl. No.: 725,957

[22] Filed: Apr. 22, 1985

[51] Int. Cl.[4] ..... C07D 271/12

[52] U.S. Cl. ..... 548/126

[58] Field of Search ..... 548/126

[56] References Cited

U.S. PATENT DOCUMENTS

| | | | |
|---|---|---|---|
| 3,163,561 | 12/1964 | Hardy et al. | 548/126 |
| 3,260,621 | 7/1966 | Shaw et al. | 548/126 |
| 3,919,224 | 11/1975 | McFarland | 548/126 |

FOREIGN PATENT DOCUMENTS

| | | | |
|---|---|---|---|
| 1211855 | 3/1966 | Austria | 548/126 |
| 205898 | 11/1984 | German Democratic Rep. | 548/126 |
| 1210604 | 10/1970 | United Kingdom | 548/126 |
| 627129 | 4/1979 | U.S.S.R. | 548/126 |
| 745901 | 7/1981 | U.S.S.R. | 548/126 |

OTHER PUBLICATIONS

March, Advanced Organic Chemistry, p. 1129 (1977).

Read, Aust. J. Chem. 38 435 (1985).

Norris, NTIS, AD-A195665, 1984.

T. P. Hobin, *Some Aminodinitro Derivatives of Benzofurazan and Benzofuroxanide,* Tetrahedron 24, pp. 6145–6148 (1968).

*Primary Examiner*—John F. Terapane

*Assistant Examiner*—J. E. Thomas

*Attorney, Agent, or Firm*—William C. Townsend; W. Thom Skeer

[57] ABSTRACT

The compound 7-amino-4,6-dinitrobenzofuroxan is synthesized by stirring monochloro-4,6-dinitrobenzofuroxan in $CH_2Cl_2$ under an ammonia atmosphere. The position of the amino group is proved by reduction with triphenylphosphine to give 7-amino-4,6-dinitrobenzofurazan, a known compound.

6 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SYNTHESIS OF 7-AMINO-4,6-DINITROBENZOFUROXAN

BACKGROUND OF THE INVENTION

1. Field of the Invention

This invention relates to the field of explosive compounds. More particularly, this invention relates to 7-amino-4,6-dinitrobenzofuroxan. Still more particularly, but without limitation thereto, this invention relates to the synthesis and characterization of 7-amino-4,6-dinitrobenzofuroxan.

2. Description of the Prior Art

The performance of warheads in ordnance systems is maximized in terms of many variables including the properties of the explosive charge. Research on energetic materials constantly seeks new explosives with superior properties for use in warheads.

The insensitive high explosive 7-amino-4,6-dinitrobenzofuroxan has a calculated explosive power superior to trinitrotoluene and equal to that of 1,3,5-triamino-2,4,6-trinitrobenzene. In that manner, it is a valuable addition to the list of energetic materials useful for warhead design.

In T. P. Hobin, *Some Aminodinitro Derivatives of Benzofurazan and Benzofuroxanide,* Tetrahedron 24, pp 6145–6148, 1968 several methods of synthesizing monoamino-4,6-dinitrobenzofurazan oxide were disclosed: thermal treatment of 3-azido-2,4,6-trinitroaniline (75% yield); and hydrolysis of benzofurazan oxide (54% yield). Both methods use expensive starting materials and the position of the amino group was not established.

SUMMARY OF THE INVENTION

An object of the present invention is to synthesize and characterize 7-amino-4,6-dinitrobenzofuroxan.

A further object of the present invention is to synthesize 7-amino-4,6-dinitrobenzofuroxan in high yield.

These and other objects have been demonstrated by the present invention wherein monochloro-4,6-dinitrobenzofuroxan in $CH_2Cl_2$ is stirred under an ammonia atmosphere to precipitate the ammonium salt of 7-amino-4,6-dinitrobenzofuroxan. Treatment with dilute HCl yields 7-amino-4,6-dinitrobenzofuroxan.

DESCRIPTION OF THE PREFERRED EMBODIMENT

This invention discloses the explosive and physical properties, synthesis and structure proof of 7-amino-4,6-dinitrobenzofuroxan:

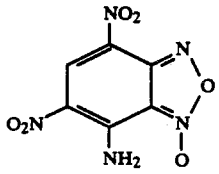

The compound 7-amino-4,6-dinitrobenzofuroxan is an insensitive, thermally stable explosive. It is a fairly dense, easily prepared compound with a calculated detonation velocity equivalent to that of 1,3,5-triamino-2,4,6-trinitrobenzene (TATB). The physical and chemical properties of 7-amino-4,6-dinitrobenzofuroxan are presented in Table 1:

TABLE 1

| PROPERTIES | MEASUREMENTS |
|---|---|
| Molecular formula | $C_6H_3N_5O_6$ |
| Molecular weight | 241.12 |
| Density | 1.902 ± 0.008 g/cm$^3$ |
| Melting point (DSC, 10°/min) | 270° (decomposition) |
| Oxygen balance (CO) | −10 |
| Percent nitrogen | 29.1 |
| Detonation velocity (calculated) | 7.91 mm/μs |
| Detonation pressure (calculated) | 282 Kbar |
| Impact sensitivity ($H_{50}$)[a] | 100 cm (TNT = 75 cm) |
| Heat of formation | +36.79 ± 0.72 Kcal/mol |

[a]Bureau of Mines design instrument, type 12 tools, 2.5 kg wt.

The introduction of an amino group into 4,6-dinitrobenzofuroxan (DNBF) has a remarkable effect upon physical and explosive properties. The melting point, density and calculated detonation velocity all increase significantly and the impact sensitivity is reduced dramatically, as is shown in Table 2:

TABLE 2

| PROPERTIES | DNBF | 7-amino-4,6-dinitrobenzofuroxan |
|---|---|---|
| Melting point | 174–175° | 270° (decomposition) |
| Density | 1.747 ± 0.001 g/cm$^3$ | 1.902 ± 0.008 g/cm$^3$ |
| Impact sensitivity | 18 cm | 100 cm |
| Detonation velocity (calc.) | 7.71 mm/μs | 7.91 mm/μs |

A synthetic approach which would apparently establish the correct structure of the monoamino-4,6-dinitrobenzofuroxan having the structure:

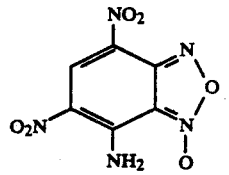

would be the treatment of 7- or 5-chloro-4,6-dinitrobenzofuroxans with ammonia to give the 7- or 5-amino-4,6-dinitrobenzofuroxans.

The monochloro-4,6-dinitrobenzofuroxan is first dissolved in an organic solvent such as methylene chloride ($CH_2Cl_2$), chloroform or benzene. The resulting solution is then stirred under an ammonia atmosphere. A solid precipitate forms, is filtered off and washed with a mineral acid such as dilute HCl or dilute $H_2SO_4$, to yield the amino product.

Treatment of either the 5-chloro or the 7-chloro compound with ammonia, yields the same product. The only distinction is in the yield amounts. The 5-chloro starting material gives a 46% yield of product while the 7-chloro compound gives a quantitative yield of 100%. This is shown by the following examples.

EXAMPLE 1

Preparation of 7-Amino-4,6-Dinitrobenzofuroxan from 7-Chloro-4,6-Dinitrobenzofuroxan A solution of 5.00 g (0.0192 mol) of 7-chloro-4,6-dinitrobenzofuroxan in 150 ml of $CH_2Cl_2$ at 25° C. is stirred under an ammonia atmosphere for 30 minutes. An orange colored solid begins separating immediately. At the end of the ammonia treatment, the orange solid is filtered off.

Stirring the solid in 100 ml of 3N HCl for 30 minutes and filtering gives 4.66 g (100% yield) of monoamino-4,6-dinitrobenzofuroxan, with a melting point of 270° C. (decomposition).

Recrystallization from $CH_3CN$ gives 3.20 g of thin gold colored plates. Recrystallization from 70% nitric acid gives orange colored tabular crystals.

Analysis calculated for $C_6H_3N_5O_6$: C, 29.89; H, 1.25; N, 29.05. Found: C, 29.87; H, 1.28; N, 28.99. A $^1H$ NMR (DMSO-$d_6$+trace HCl, 30°) spectrum shows peaks at δ10.10, 9.45 ($NH_2$, s, nonequivalent); 9.00 (H-5, s). A $^{13}C$ NMR (DMSO-$d_6$, TMS standard) spectrum shows peaks at δ120.4 (C-4, s); 132.5 (C-5, s); 121.6 (C-6, s); 142.8 (C-7, s); 110.9 (C-8, s); 146.2 (C-9, s).

EXAMPLE 2

Preparation of 7-Amino-4,6-Dinitrobenzofuroxan from 5-Chloro-4,6-Dinitrobenzofuroxan A solution of 0.562 g (0.00216 mol) of 5-chloro-4,6-dinitrobenzofuroxan in 25 ml of $CH_2Cl_2$ is cooled to −10° C. and treated with gaseous $NH_3$, with stirring. An orange colored solid separates immediately. After 10 minutes, the suspended solid appears orange-red in color and the liquid phase is likewise orange-red in color.

The solid is filtered off and stirred in 50 ml of 3N HCl at 25° C. to give 0.237 g (46% yield) of a tan powder with an infrared spectrum identical to that of the product of Example 1.

Examples 1 and 2 establish that the same product was formed regardless of the starting material. However, molecular rearrangement may occur in compounds with a nitro group adjacent to a furoxan ring which interconverts the 5 and 7 positions. Thus, an approach other than simple substitution is required to establish the position of the amino group in monoamino-4,6-dinitrobenzofuroxan. While a furazan ring is not convertible to a furoxan ring, the latter is readily reduced to yield a furazan ring. In this manner, reduction prevents isomerization.

To aid in characterization, 7-amino-4,6-dinitrobenzofurazan is independently synthesized by a known method as is shown by the following example.

EXAMPLE 3

Synthesis of 7-Amino-4,6-Dinitrobenzofuroxan

A solution of 0.595 g (0.00232 mol) of 7-methoxy-4,6-dinitrobenzofurazan in 10 ml of $CH_2Cl_2$ at 25° C. is stirred under an ammonia atmosphere for 10 minutes. An orange-yellow colored solid begins separating immediately.

Volatiles are removed on a rotary evaporator to leave 0.565 g of the ammonium salt of 7-amino-4,6-dinitrobenzofurazan. This is stirred for 10 minutes in 50 ml of 1N HCl, filtered, washed and dried to give 0.485 g (93% yield) of 7-amino-4,6-dinitrobenzofurazan. Recrystallization from $CH_3CN$ yields 0.353 g of 7-amino-4,6-dinitrobenzofurazan, with a melting point of 249°–253° C. (decomposition).

Analysis calculated for $C_6H_3N_5O_5$: C, 32.01; H, 1.34; N 31.11. Found: C, 32.02; H, 1.39; N, 31.04. A $^1H$ NMR (DMSO-$d_6$+trace HCl, 40° C.) spectrum shows peaks at δ10.91, 10.08 ($NH_2$, s, nonequivalent); 9.08 (H-5, s).

Reduction of the monoamino-4,6-dinitrobenzofuroxan product of examples 1 and 2 is achieved by mixing the monoamino compound with triphenylphosphine, a reducing agent. An organic solvent is used and the solution is heated to reflux, about 140° C. Suitable solvents are benzene and toluene, however due to their low boiling points, reflux must be done under pressure in order to reach 140° C. without vaporization. The preferred solvent is xylene, since it can be used at atmospheric pressure. This reduction process is illustrated in Example 4.

EXAMPLE 4

Reduction of Monoamino-4,6-Dinitrobenzofuroxan to its Corresponding Furazan

A mixture of 0.500 g (0.00207 mol) of monoamino-4,6-dinitrobenzofuroxan and 5.45 g (0.027 mol) of triphenylphosphine in 50 ml of xylene is heated to reflux for 10 minutes. The reaction mixture, upon heating, immediately turns dark brown in color and brown gas ($NO_2$) appears in the condenser.

Reaction products are separated by chromatography on a 35×210 mm silica gel column using $CH_2Cl_2$ as the developing solvent. Following unreacted triphenylphosphine there are three major bands.

The first band collected gives 2.0 g of a red solid. Recrysystallization from $CCl_4$ gives red needles of 2-(triphenylphosphinimido)-4,6-dinitroaniline with a melting point of 235°–236° C. Analysis calculated for $C_{24}H_{19}N_4O_4P$: C, 62.88; H, 4.18; N, 12.22; P, 6.76. Found: C, 62.61; H, 4.25; N, 12.05; P, 7.04.

The second band collected gives 0.083 g of 7-amino-4,6-dinitrobenzofurazan. The infrared spectrum of this material is identical to the infrared spectrum of the separately synthesized (example 3) 7-amino-4,6-dinitrobenzofurazan.

The third band to be collected gives 0.10 g of triphenylphosphine oxide, with a melting point of 156°–157° C.

The above mentioned second band results establish that the amino group is in the 7 position, regardless of whether the starting material is 5-chloro or 7-chloro-4,6-dinitrobenzofuroxan.

There was uncertainty as to a possible retro-Boulton-Katritzky rearrangement of 7-amino-4,6-dinitrobenzofuroxan at 140° C., the temperature of the reduction reaction, which conceivably could give the isomeric reduction product. See P. B. Ghosh, *Preparation and Study of Some 5- and 7-Substituted 4-Nitrobenzofurazans and Their N-Oxides; A Retro-Boulton-Katritsky,* Journal of the Chemical Society (B), pp 334–338 (1968). However, thermal analysis of 7-amino-4,6-dinitrobenzofuroxan indicates a straight heat flow versus temperature trace from 25° to 240° C. which means that at least in the solid phase, there is no retro-Boulton-Katritzky rearrangement occurring below 340° C. and definitely not at 140° C. The aforementioned uncertainty is thus virtually eliminated.

This invention has been described in detail with particular reference to certain preferred embodiments thereof, but it will be understood that variations and modifications can be effected within the spirit and scope of the invention.

What is claimed is:

1. A method of synthesizing 7-amino-4,6-dinitrobenzofuroxan comprising the steps of:

placing monochloro-4,6-dinitrobenzofuroxan in solution with an organic solvent;

stirring said solution under an ammonia atmosphere;

precipitating an orange colored solid;

separating said solid by filtration; and washing said solid with a mineral acid and filtering to yield the product, 7-amino-4,6-dinitrobenzofuroxan.

2. The method claim 1 wherein said monochloro-4,6-dinitrobenzofuroxan is selected from the group consisting of: 5-chloro-4,6-dinitrobenzofuroxan and 7-chloro-4,6-dinitrobenzofuroxan.

3. The method of claim 1 wherein said organic solvent is selected from the group consisting of: methylene chloride, chloroform and benzene.

4. The method of claim 3 wherein said organic solvent is methylene chloride.

5. The method of claim 1 wherein said mineral acid is selected from the group consisting of: HCl and $H_2SO_4$.

6. The method of claim 5 wherein said mineral acid is HCl.

* * * * *